United States Patent [19]

Nooning

[11] Patent Number: 5,393,227
[45] Date of Patent: Feb. 28, 1995

[54] DENTAL IMPRESSION HANDLING TOOL AND METHOD

[75] Inventor: William H. Nooning, Westminster, Colo.

[73] Assignee: KeyPro Innovations, Inc., Denver, Colo.

[21] Appl. No.: 201,826

[22] Filed: Feb. 25, 1994

[51] Int. Cl.$^6$ ............................................. A61C 19/00
[52] U.S. Cl. ................................... 433/74; 433/213
[58] Field of Search ...................... 433/34, 60, 74, 213

[56] References Cited

U.S. PATENT DOCUMENTS

| | | | |
|---|---|---|---|
| 2,619,725 | 12/1952 | Roeser . | |
| 2,700,218 | 1/1955 | Lindley | 433/213 |
| 2,700,219 | 1/1955 | Lindley | 433/60 |
| 2,786,272 | 3/1957 | Lindley | 433/60 |
| 3,581,398 | 6/1971 | Thomas . | |
| 3,702,027 | 11/1972 | Marshall et al. | 433/34 |
| 3,838,187 | 9/1974 | Thomas . | |
| 3,937,773 | 2/1976 | Huffman | 433/213 |
| 4,059,902 | 11/1977 | Shiokawa | 433/34 |
| 4,116,416 | 9/1978 | Segura | 433/34 |
| 4,200,981 | 5/1980 | Fine | 433/60 |
| 4,203,219 | 5/1980 | Wiener | 433/74 |
| 4,265,619 | 5/1981 | Lucki et al. | 433/54 |
| 4,283,173 | 8/1981 | Browne et al. | 433/34 |
| 4,368,042 | 1/1983 | Felstead et al. | 433/213 |
| 4,398,884 | 8/1983 | Huffman | 433/74 |
| 4,439,151 | 3/1984 | Whelan | 433/60 |
| 4,459,110 | 7/1984 | Jackson | 433/74 |
| 4,492,578 | 1/1985 | Hann et al. | 433/213 |
| 4,508,506 | 4/1985 | Jackson | 433/74 |
| 4,538,987 | 9/1985 | Weissman | 433/60 |
| 4,608,016 | 8/1986 | Zeiser | 433/74 |
| 4,708,835 | 11/1987 | Kiefer | 264/17 |
| 4,767,330 | 8/1988 | Burger | 433/213 |
| 4,898,359 | 2/1990 | Gopon | 433/74 |
| 5,125,833 | 6/1992 | Berceaux | 433/74 |
| 5,129,822 | 7/1992 | Dobbs | 433/74 |
| 5,197,874 | 3/1993 | Silva et al. | 433/74 |

*Primary Examiner*—Cary E. O'Connor
*Attorney, Agent, or Firm*—Hancock & Knearl

[57] ABSTRACT

A dental impression handling tool consists of two base structures shaped to approximate two opposite quadrants of a full dental arch, and two similarly-shaped inserts that snap fit into the base structures. Each base includes a wide, upward facing trough approximating the placement and curvature of teeth within a dental quadrant. The upper surface of each insert is attached to a positive dental mold by means of protrusions that extend from the top horizontal surface of the insert, the protrusions being encased within the mold material. Positive positional relationship is maintained between each base and its mating insert by the use of an interlocking and non-recurring geometric pattern that is carried by the internal vertical walls of the trough in the base, and by a matching geometric pattern that is carried by the outer vertical walls of two vertically downward extending ribs on the underside of the insert. A second deeper, narrower and centrally located trough is formed in each base. This second trough mates with a third center rib that protrudes from the bottom surface of each insert. The insert's center rib contains a retainer bead along both vertical side walls. This bead provides a snap-lock fit into a corresponding negative indentation formed along the vertical side walls of the center trough in each base. The center rib in each insert contains cylindrical cavities which allow the insertion of standard dental dowels or suitable substitutes.

17 Claims, 7 Drawing Sheets

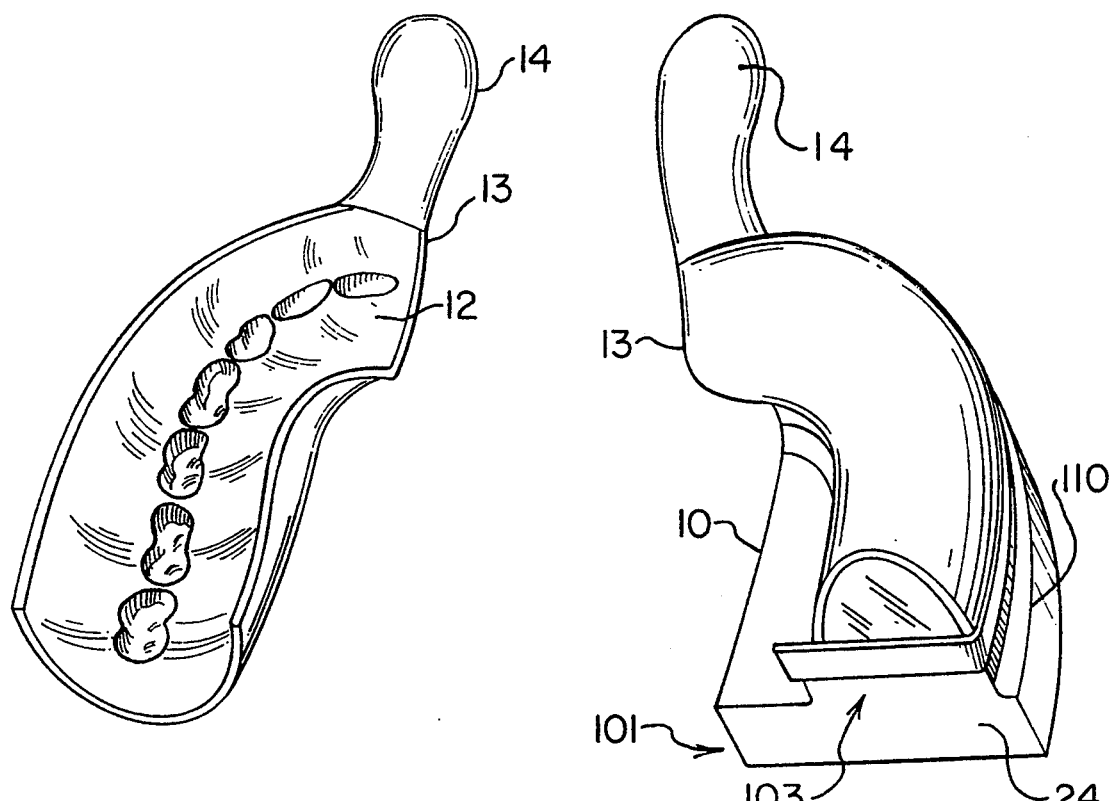
FIG. 9
FIG. 10
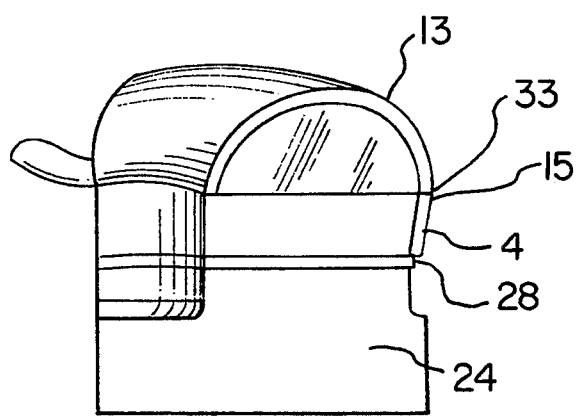
FIG. 11

DENTAL IMPRESSION HANDLING TOOL AND METHOD

BACKGROUND OF THE INVENTION

1. Field of the Invention

This invention relates to the field of dentistry and more specifically to work support apparatus having guide and positioning means.

2. Description of the Prior Art

The devices and techniques used thus far in the art of dental impression handling tools and the like have required a mold process to be performed by a dental technician. Various types of devices/procedures have been used, with all of them generally falling into three categories.

The first, and most widely used type of device/procedure, involves the use of some form of positioning pins or rods which are inserted into the molds, with the molds then being positioned on a base. The base is most generally made of the same material as the mold. This method is time consuming and relatively difficult to perform. Some of the steps which may be required in order to construct a model are: Drilling the model, pouring a plaster base, inserting pin sleeves into the base material before hardening, and repairing the model due to sawing into improperly placed pins.

The second type of device/procedure involves pouring mold material into a negative impression, and a pre-formed base, or mold, form having a channel or indented cavity. In this method, the mold material is cast so as to form an indexing pattern. Once the mold has hardened, it is removed from the form base so that saw cuts can be made in the model. The model is then re-assembled into the pre-formed base. While this method requires less time than the previously-described method, the accuracy of indexing deteriorates with each removal and re-insertion of the model into the pre-formed base, and attachment of the model to the base requires either a manual locking mechanism, or a chemical application.

Both of these first two types of devices/procedures have the added disadvantage of having to "construct" the "bite" after the opposing jaw models have been removed from the negative impression.

The third type of device/procedure generally incorporates a base and a set of pre-established positioning element(s). The positioning element(s) fit into the base by using rods, or tabs, that protrude from the underside of the positioning element(s), and fit into holes or slots in the base. While this arrangement takes less casting time and provides more consistent alignment, it has some significant drawbacks. Generally, this arrangement requires that either the negative impression be precisely aligned to the positioning elements at the time of mold casting, or that the mold be chemically attached to the positioning elements after the mold has been removed from the negative impression. Devices that do not require either of the above require the mold to be removed from the base in order to permit sawing through the mold.

All of the prior art arrangements require that the methods thereof be performed by a skilled technician in order for the device/procedure to function properly.

SUMMARY OF THE INVENTION

This invention relates to dental impression handling tools and methods, such as are used in the production of molded dental models. As is well known, dental models of this type are used in the manufacture of crowns, bridges, and other dental prosthetics.

The invention basically consists of two base structures that are shaped to approximate two opposite quadrants of a full dental arch, and two similarly designed inserts that fit into the two base structures with great positional accuracy. The base and insert members are embodied as right hand and left hand pairs, each pair comprising one base and one insert.

Each base member includes a wide, upward facing, trough or channel which approximates the placement and curvature of teeth within a dental quadrant. The upper surface of each insert member is attached, preferably permanently attached, to a positive dental mold by means of protrusions that extend from the top horizontal surface of the insert, the protrusions being encased within the mold material after the mold material has hardened.

Accurate positive positional relationship is maintained between each base member and its mating insert member through the use of an interlocking and non-recurring geometric pattern that is carried by, or formed in, the internal vertical walls of the trough in the base member, and by matching reverse geometric patterns that are carried by the outer vertical walls of two vertically downward extending ribs that are formed on the underside of each insert member.

A second deeper and narrower centrally-located trough is formed in each base member. This second trough mates with a third center rib that protrudes downward from the bottom surface of each insert. This second trough extends generally the full length of the underside of its insert member. Each insert's center rib contains a retainer bead along both vertical side walls thereof. This bead provides a positive, snap-lock fit into a corresponding negative indentation that is formed along the vertical side walls of the center trough in each base member.

The center rib in each insert member contains cylindrical cavities which allow the insertion of standard dental dowels or suitable substitutes. These dowels provide a dental technician with a "working handle" so that an isolated dental tooth impression can be easily manipulated.

The invention provides for the construction of a dental model in a single pour procedure, decreases the time that is needed to construct the model, eliminates the need for technician involvement with the model-making process, and accepts a variety of mold mediums, the most common mold medium being plaster of paris.

These and other objects, advantages, and features of the invention will be apparent to those of skill in the art upon reference to the following detailed description of preferred embodiments of the invention, which description makes reference to the drawing.

BRIEF DESCRIPTION OF THE DRAWING

FIG. 9 is a top prospective view of a quadrant arch negative dental impression positioned in a conventional single-sided impression tray.

FIG. 10 is a bottom prospective view of the impression tray of FIG. 9 after the impression tray has been filled with dental mold material, and with the impression tray inverted and then placed on the assembled right insert member and right base member of FIG. 7.

FIG. 11 is a view taken from the rear vertical wall side of the assembly of FIG. 10.

FIG. 15 shows two facing posts of one circular configuration, and shows that each post has a vertically-extending outside wall, a horizontal top wall, and an inner wall that is tapered five degrees to the horizontal.

DESCRIPTION OF THE PREFERRED EMBODIMENT

A dental impression handling tool in accordance with the invention is basically composed of four components: A left insert member 104 shown in FIG. 1, a right insert member 103 shown in FIG. 2, a left base member 102 shown in FIG. 4, and a right base member 101 shown in FIG. 5. The two base members and the two insert members are preferably made of plastic resin material that retains its rigidity in thin-wall construction, while being able to be easily manually cut by a saw blade. A non-limiting example of a usable resin material is medium impact styrene; i.e., a polymerized thermoplastic styrene resin, i.e., polystyrene.

Figure 5:
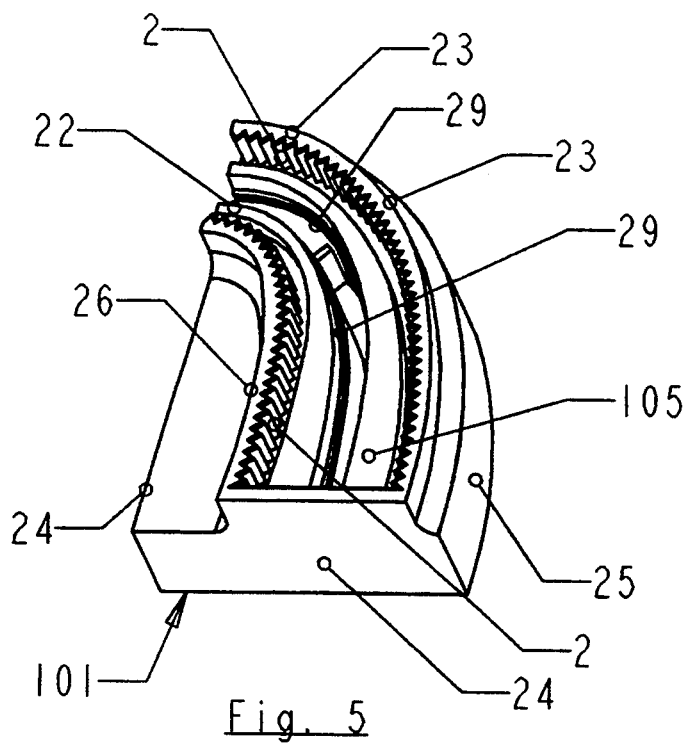
FIG. 5 is a top prospective view of the right base member of the invention, these figures showing first and second troughs that are formed in the top horizontal surface of each base member, the internal vertical walls of the first wide trough carrying an interlocking, non-reoccurring, geometric pattern that mates with the geometric pattern of the insert members, and the second narrower and deeper trough mating with the center rib of the insert members, this second trough also carrying a negative indentation that snap locks with the retainer bead of the insert members.
Figure 4:
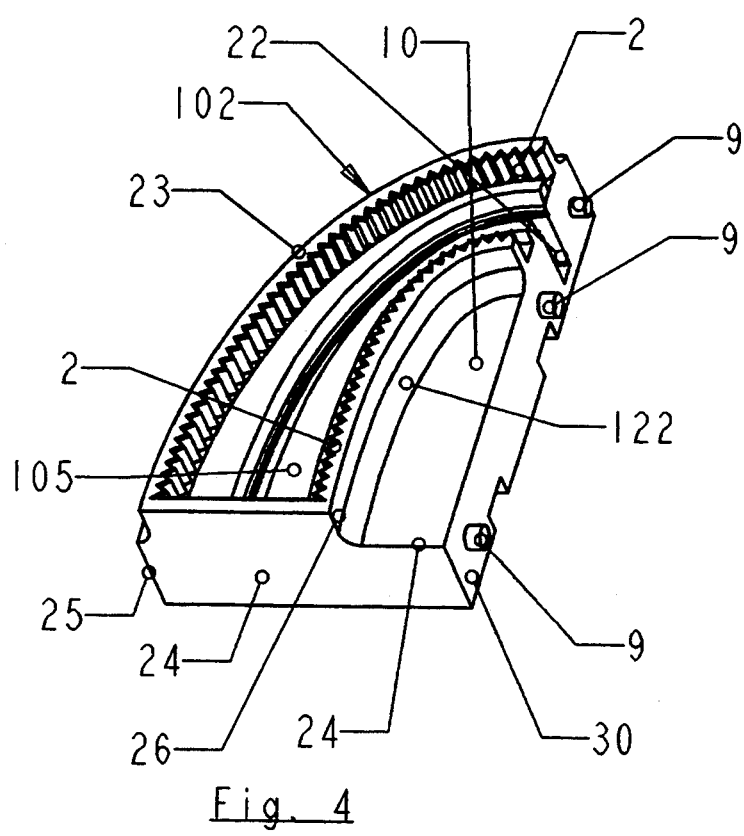
FIG. 4 is a top prospective view of the left base member of the invention.

The two bases 101,102 are constructed and arranged, as is shown in FIGS. 4 and 5, with each base having an outer curved wall 23 that extends vertically upward from a relatively thick horizontal portion 24 of the base. Walls 23 extend along the outside curved portion 25 of each base. A vertical inner wall 26 extends upward from horizontal base portion 24, and runs non-parallel to outer wall 23.

Figure 3:
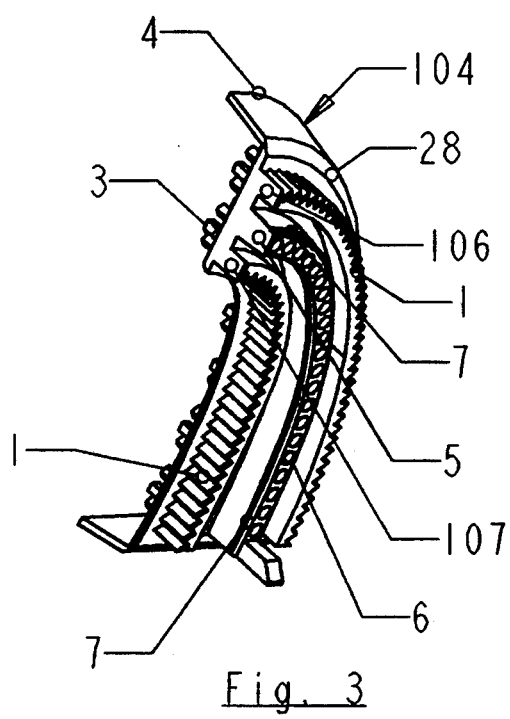
FIG. 3 is a bottom prospective view of the left insert member of FIG. 2, showing the three ribs that extend vertically downward from the bottom surface of each insert member, the two outer ribs each carrying an interlocking, non-reoccurring, geometric pattern on the outer walls thereof, the center rib carrying a retainer bead on both of the outer walls thereof, and the center rib carrying cylindrical cavities allowing dental dowels to be inserted therein.
Figure 6:
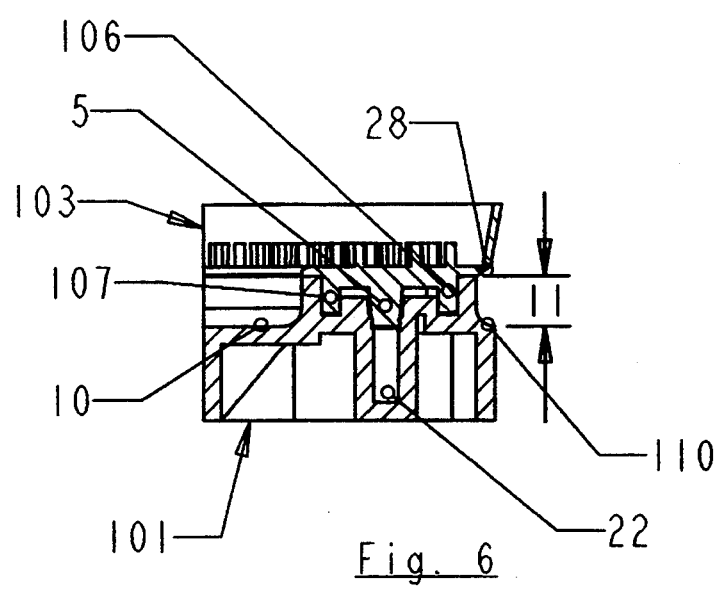
FIG. 6 is a cross-sectional view of the right insert member of FIG. 2 and the right base member of FIG. 5 after assembly.

The internally-facing vertical sides of walls 23,26 of each base form the inside vertical walls of a first relatively wide and tapered trough 105 in the two bases 101,102. The inside walls of trough 105 are constructed and arranged to provide two non-recurring geometric tooth patterns 2 which form a continuous, irregular, non-repeating surface that extends along the inside walls of trough 105. Patterns 2 extend vertically down the inside surfaces of walls 23,26 a finite distance, and provide an "indexing" function when the matching pattern 1 of an insert is mated with the matching tooth pattern 2 of a base, as is shown in FIG. 6. As shown in FIGS. 3 and 6, these tooth patterns 1 are carried by the outside surfaces of a first and a second non-parallel rib 106,107 that extend down from the surface of each insert. Inserts 103,104 fit precisely into trough 105 of a respective base 101,102, with the depth of the pattern 2 in the base approximating the height of the pattern 1 in its mating insert. The arcuate shape of ribs 106,107 is substantially identical to the mating arcuate shape of walls 23,26.

The inner curved wall 26 of each base 101,102 preferably meets horizontal base surface 10 by way of a curved, or slanted, surface 122. This construction and arrangement provides easy manual removal of excess dental stone at the time of pour up, and eliminates a buildup of stone in this corner portion of the base.

Figure 14:
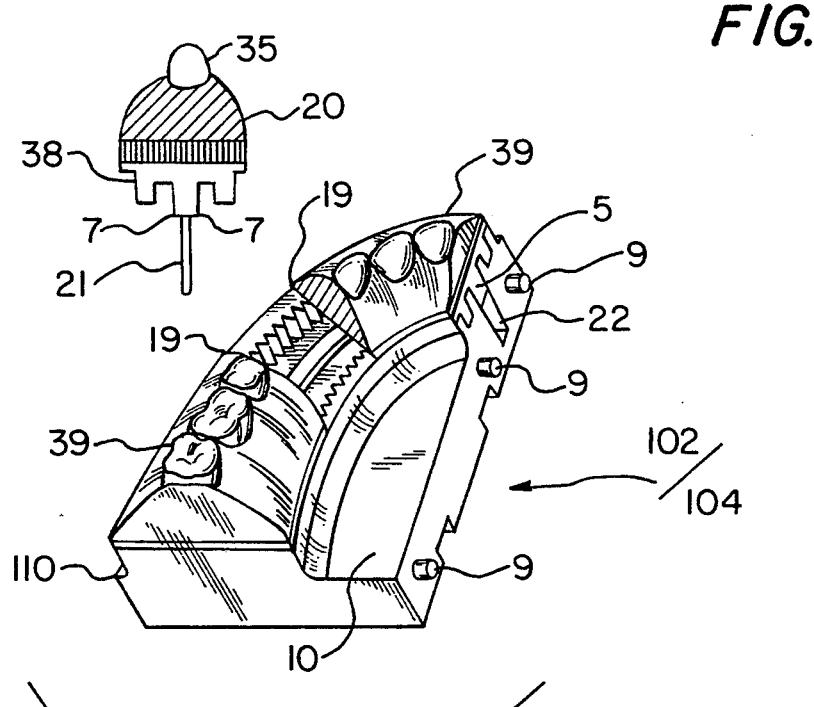
FIG. 14 is a top prospective view of a dental model and the left member insert member and left base member assembly of FIG. 12, and showing a section of the dental model that has been isolated and removed from the remained of the dental model by sawing through the dental model and the left insert member while the left insert member was positioned on the left base member.

Due to the above-described unique construction and arrangement of continuous, irregular, non-repeating surface patterns 1,2, and due to the manner in which walls 23,26 do not run parallel (for example, walls 23,26 converge as shown in FIGS. 4 and 5), there is only one way or position in which an insert 103,104 fits onto its corresponding base 102,101. Also, when a section of tooth 20 is cut away, as shown in FIG. 14, there is only one way or position in which this section 20 will fit back into the base, independent of how thin section 20 may be. While the details of construction of tooth patterns 1,2 are not critical to the invention, in a preferred embodiment, the angle of the tooth sides did not repeat along the length of patterns 1,2, such that there was only one position of tooth match. Also, while the details of construction of walls 23,26 is are not critical to the invention, in a preferred embodiment, walls 23,26 were made to be non-parallel by forming the walls as converging walls formed of radius sections having progressively smaller radius as the walls converged, such that there was only one position of wall match.

Figures 1, 2:
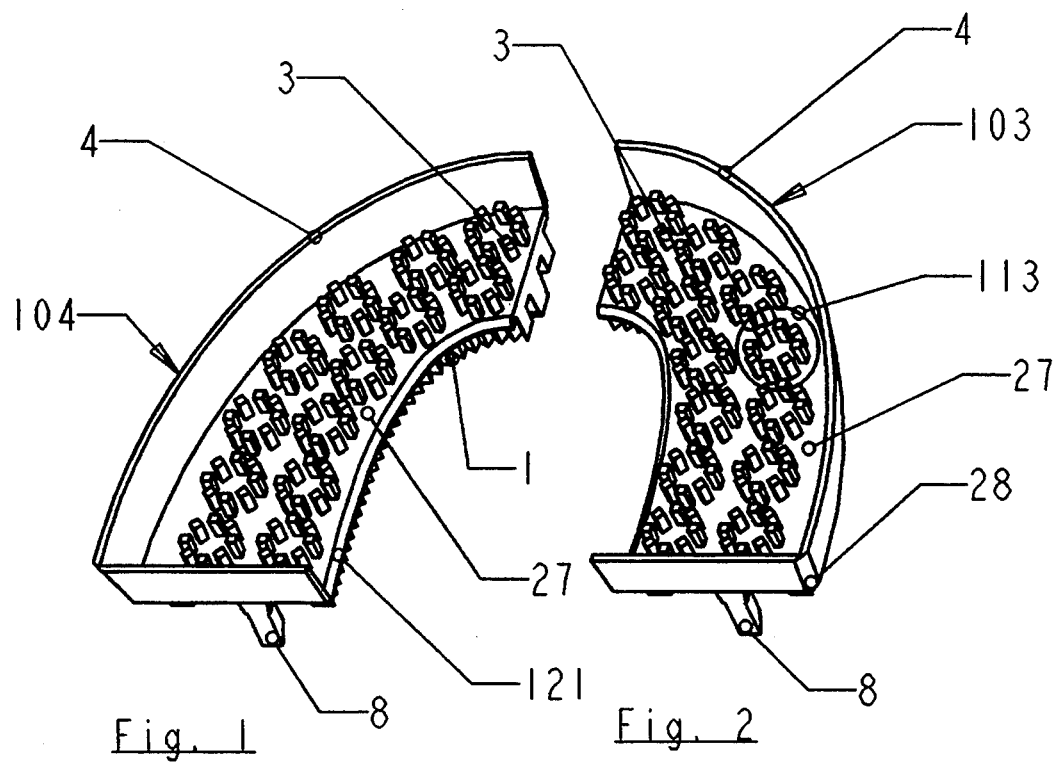
FIG. 1 is a top prospective view of the left insert member of the invention showing the vertically-extending anchoring members that are carried by the top horizontal surface of the left insert member, and showing a removable retaining wall that boarders portions of the top horizontal surface.
FIG. 2 is a top prospective view of the right insert member of the invention showing the vertically-extending anchoring members that are carried by the top horizontal surface of the right insert member, and showing a removable retaining wall that boarders portions of the top horizontal surface.

Each insert 104,103 of FIGS. 1 and 2 has a number of vertically-extending anchoring members 3 extending upward from its top horizontal surface 27. Anchoring members 3 extend generally continuously along the surface length of each insert 103,104. While the details of construction of anchoring members 3 are not critical to the invention, it is preferred that each of the anchoring members 3 include a geometric pattern or surface that assures the permanent bonding of anchoring members 3 with dental mold material, to thereby prevent vertical separation, as well as longitudinal slippage of the dental mold relative to the insert members. FIGS. 1 and 2 illustrate one preferred embodiment of anchoring members 3.

Figure 15:
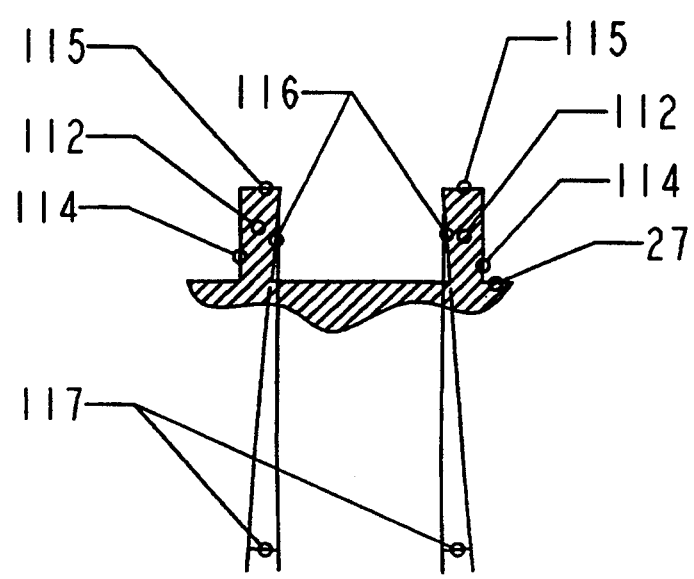
FIG. 15 shows an embodiment of the anchoring members of FIGS. 1 and 2 which comprises thirteen circular post configurations, each circular configuration containing eight individual vertically-extending posts.

A preferred embodiment of anchoring members 3, as shown in FIG. 2, provides about thirteen circular configurations 113, each of which contains about eight individual vertically-extending posts 112. FIG. 15 shows a portion of the horizontal surface 27 of FIG. 2 in section view, the section view being taken through the center of a circular configuration 113. FIG. 15 shows two facing posts 112 of circular configuration 113. For purposes of clarity, the three posts 112 that are not cut away in FIG. 5 have not been shown. Each post 112 includes a vertically-extending outside wall 114, a horizontal top wall 115, and an inner wall 116 that is tapered about five degrees to the horizontal; i.e., angle 117 (exaggerated in FIG, 15) is about five degrees.

The plurality of post configurations 113 are adapted to secure the dental model to the insert member 103,104. Each one of the post configurations 113 comprises a plurality of individual posts 112 that extend in a generally vertically upward direction from top surface 27 of the insert member. The individual posts 112 of a configuration 113 are arranged to form a closed curve, such as a circle. Each individual post 112 in a configuration 113 has a top surface 115, and an inner surface 116 that faces the inner surfaces 116 of the other individual posts 112 in its configuration 113, and the inner surfaces 116 extend at an angle to the vertically-upward direction, so as to define a circle of a small diameter adjacent to the top surface 115 of said posts, and a circle of a large diameter adjacent to the top surface 27 of the insert member.

Figure 12:
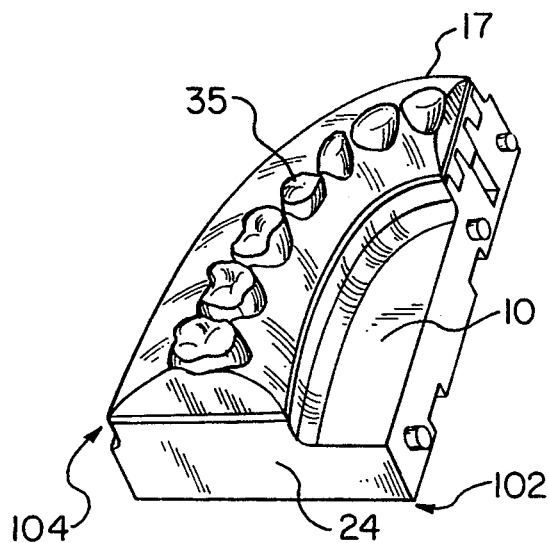
FIG. 12 is a top perspective view of a positive dental model affixed to an assembly of the left insert member of FIG. 1 and the left base member of FIG. 4 after the impression tray and the insert member's retaining wall have both been removed.
Figure 13:
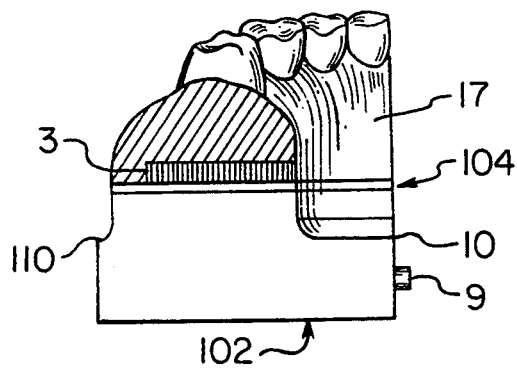
FIG. 13 is a cross-sectional view of FIG. 12 showing the dental stone interlocked with the vertical anchoring members of the left insert member.

A generally vertical and manually-removable retaining wall 4 extends upward from the generally flat and horizontal surface 27 of each insert 103,104. Wall 4 extends along the outside edge of each insert, and is designed to act as a guide for the placement of a dental impression tray 13, of the general type shown in FIG. 9, on the insert. Wall 4 also acts as a flow retainer for flowable dental model material. Retaining wall 4 is provided with a chamfer 28 best seen in FIG. 11. Chamfer 28 allows wall 4 to be manually-separated from the assembled insert and base by "peeling" retaining wall 4 off of the assembled insert and base after the positive dental model material has hardened, as illustrated in FIGS. 12 and 13.

A third center rib 5 extends downward from the bottom of each insert 103,104, as best seen in FIGS. 3 and 6. Cylindrical cavities or holes 6 extend vertically upward into rib 5 along generally the entire length of rib 5. Cylindrical cavities 6 allow for the insertion of a standard dental dowel pin 21, or suitable substitute, best seen in FIG. 14.

Positive snap-lock retainer beads 7 (FIG. 3) extend along the inside and the outside length of ribs 5. Beads 7 fit into corresponding negative indentations 29 (FIG. 5) that are formed in a second narrow trough 22 of base members 101,102. The mechanical cooperation of beads 7 and indentations 29 provide a positive lock, snap-fit retaining mechanism which secures each insert 103,104 into its mating base 101,102.

Figure 7:
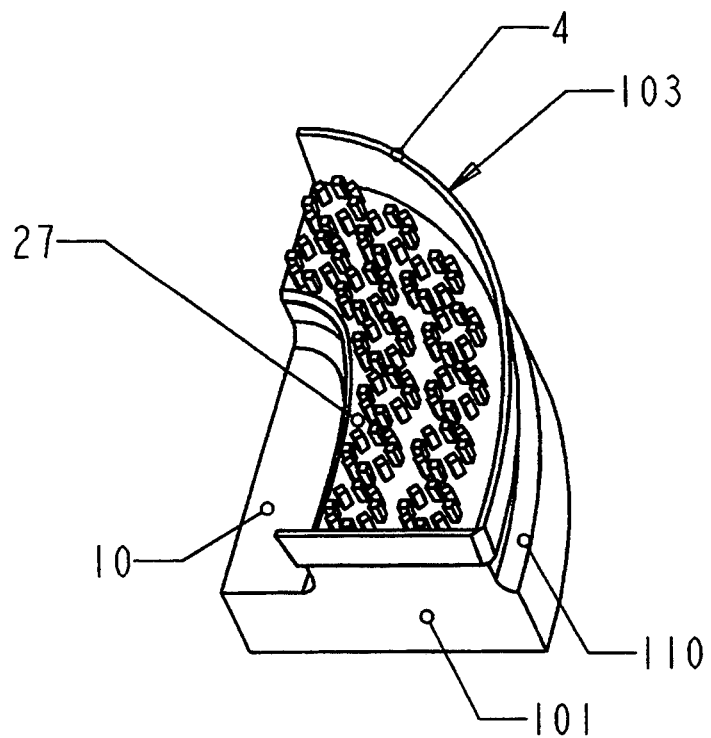
FIG. 7 is a top prospective view of the right insert member of FIG. 2 and the right base member of FIG. 5 after assembly.

An alignment post 8 projects vertically down from the posterior end of each rib 5. Alignment posts 8 provide easy mating of an insert to its mating base, and provide for the proper positioning of the insert in relation to the base, during assembly of an insert/base to their mating position shown, for example, in FIG. 7.

The inside edge 121 of each insert 103,104 is preferably rounded, or sloped, to aid in the flow of excess dental stone off of the insert, and to aid in the manual removal of excess stone.

Figure 8:
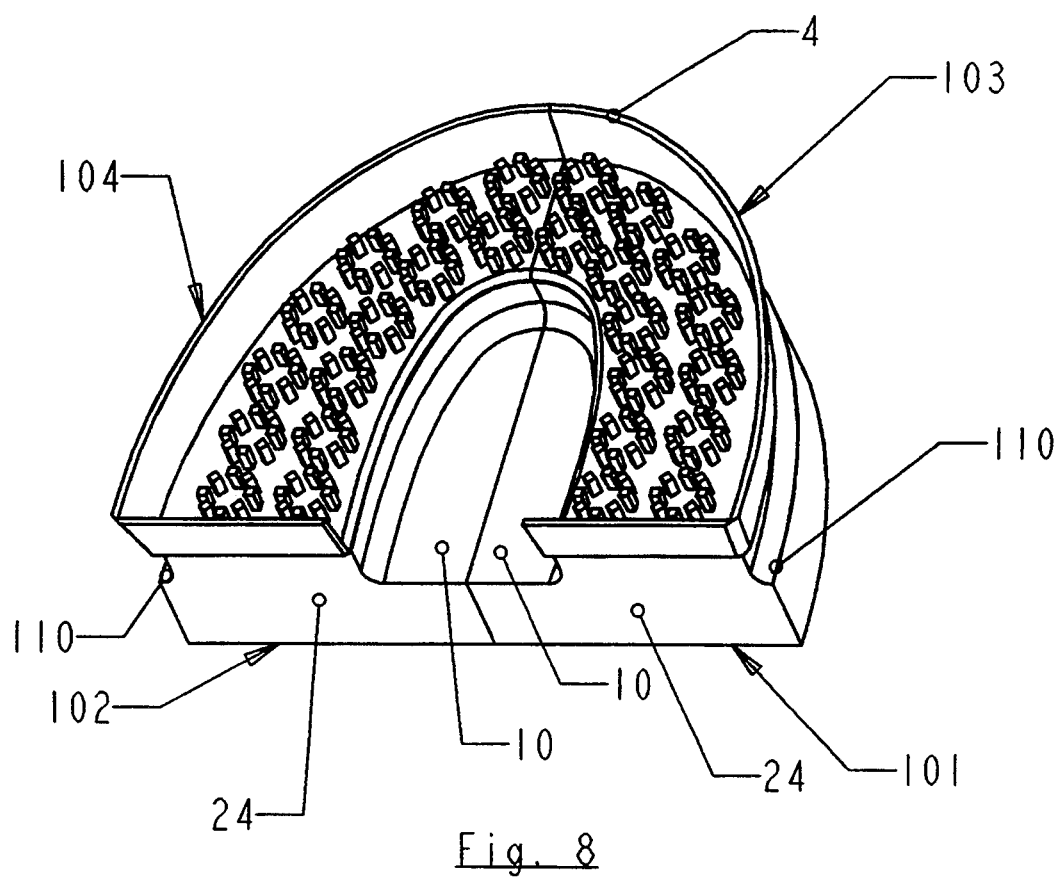
FIG. 8 is a top prospective view of the left and right insert members of FIGS. 1 and 2, and the left and right base members of FIGS. 4 and 5 after assembly to form a full arch.

As shown in FIGS. 4 and 5, left-hand base 102 and right base 101 have mating geometric male/female patterns 9 that are formed along their adjacent mid-line and vertically extending walls 30. Patterns 9 allow bases 101,102 to be joined to form a full lower or full upper dental arch when the two bases are abutted and bonded together, as is shown in FIG. 8. Geometric patterns 9 are constructed and arranged to allow only one possible abutment position. Bases 101,102 can be bonded in the FIG. 8 position through the use of chemical, mechanical or thermal means. FIGS. 4 and 5 illustrate one non-limiting embodiment of geometric patterns 9 which consists of three alignment pins of unequal sizes and/or diameters that mate with corresponding sized alignment holes that are formed in right base 101. For example, the center one of pins 9 and one of the outer located pins 9 are of equal size, whereas the remaining pin 9 is of a smaller size.

The rear vertical sides and the horizontal undersides of base members 101,102 are preferably designed so as to allow attachment of a variety of articulators, as is well known to those of skill in the art.

Incorporated into each base 101,102 are horizontal saw cut indicator planes 10 and matching height saw cut indicator planes 110; for example, see FIG. 8. As seen in FIG. 6, the depth 11 of each insert 103,104 is precisely aligned and designed for sawing of an insert while the insert is mated with a base. Sawing vertically down to saw cut indicators 10,110 in FIG. 6 allows segmentation of insert 103 without destroying the mechanical integrity of base 101. This segmentation is illustrated in FIG. 14.

FIG. 9 illustrates a typical single-sided quadrant arch negative impression 12 which is supported and carried by a plastic impression tray 13 having a handle 14. A well-known process of constructing the positive dental model 17 of FIGS. 12 and 13 from the negative impression 12 of FIG. 9 is accomplished by first trimming excess impression material from negative impression 12. Negative impression 12 is then filled with dental stone or epoxy, and a layer of dental stone or epoxy is applied to the top horizontal surface 27 of insert 103 (see FIG. 7). The negative impression 12 is then inverted onto the assembled insert 103 and base 101 as shown in FIG. 10. This procedure ensures that anchoring members 3 of insert 103 are embedded in the mold medium as shown in FIG. 13.

As mentioned, retaining wall 4 is used as a guide for positioning impression tray 13 as above described. As shown in FIG. 11, this is accomplished by aligning the top 15 of retaining wall 4 with the bottom 33 of impression tray 13, generally following the curvature of tray 13 and retaining wall 4. Excess stone or epoxy is then manually removed.

Once this first model of the impression has hardened, the same process can be repeated with the opposing side of the impression. When using a two-sided impression tray, this opposing model can be made with or without removal of the first model 17 from its negative impression 12. If the second impression is made without removing the first model 17, an appropriate articulator is attached to the bases 101,102. This permanently establishes the correct interrelationship of the upper and lower teeth; i.e., "the bite", without requiring manual alignment. If the first model 17 is removed from the negative impression 12, the relative position of the opposing model; i.e., "the bite", can easily be re-established when the second mold has hardened by inserting the first model 17 back into negative impression 12, and then attaching an appropriate articulator.

After the dental stone or epoxy has hardened, the hardened material forms a positive model 17 which is permanently attached to an insert by the interlocking of the hardened mold material and anchoring vertical members 3, as shown in FIG. 13. Once an articulator has been affixed to bases 101,102, the dental model is ready to be used to construct a prosthesis.

Construction of the prosthesis begins by isolation of the tooth or teeth 35 (see FIG. 14) for which the prosthesis will be constructed from the remaining teeth 39. This is accomplished by sawing down through mold or model 17 and insert 104 on both sides of the teeth, or tooth model 35 which will receive the prosthesis. Saw cuts are made down to the depth of indicators 10,110 in base 102, and are sufficiently deep to completely cut through insert 104 without cutting through base 102. Once the appropriate saw cuts 19 have been made, the section of teeth 20 which was isolated is removed from base 102, as shown in FIG.14, and a dowel pin 21 is inserted and affixed into the appropriate cylindrical cavity 6 to allow ease of manipulation during construction of the prosthesis.

Upon reinsertion of the isolated teeth 20 into base 102, dowel pin 21 therein remains permanently affixed to isolated insert portion 38 through the use of the second narrow trough 22 that extends along the arc of base 102, as shown in FIGS. 4, 5 and 6. Once the teeth have been isolated, as shown at 20, section 20 can be easily removed from and re-inserted into base 102 multiple times without deterioration of the relative positioning of the teeth to the remainder 39.

The repetitive and positive positioning that is accomplished by the invention results from a synergetic interaction of a number of key factors; for example, the rigidity of the material from which bases 101,102 and inserts 103,104 are made, the use of mating and non-recurring geometric patterns 1, 2 and 9, the rigidity that is provided by the use of three insert ribs 5,106,107 that mate with two troughs 22,105 that are formed in the base, the use of a positive snap-fit retaining mechanism 7,29 which secures each insert into its matching base, and the positive locking action of the mold medium to the anchoring members 3 of each insert once the mold medium has hardened.

While the invention has been described in detail while making reference to preferred embodiments thereof, it is recognized that those skilled in the art will readily visualize yet other embodiments that are within the spirit and scope of the invention. Thus, the forgoing description is not to be taken as a limitation on the invention.

What is claimed is:
1. Dental impression handling apparatus, comprising;
a base member having a top surface and a bottom surface that is vertically spaced downward from said top surface,
first and second horizontally spaced, generally non-parallel, and arcuate-shaped walls extending vertically upward from a position that is vertically above said bottom surface to said top surface, said first and second walls defining a first arcuately-shaped trough in said top surface of said base member, said first and second walls having at least one wall surface extending generally vertically upward and generally perpendicular to said top surface,
an interlocking and non-recurring geometric pattern formed in said at least one wall surface of said first and second walls,
an insert member adapted to be mounted to engage said top surface of said base member, said insert member having a top surface adapted to support a dental model and having a bottom surface that is vertically spaced downward from said top surface,
first and second horizontally spaced, generally non-parallel, and arcuate-shaped ribs extending vertically downward from said bottom surface of said insert member, said ribs approximating the arcuate shape of said first and second walls and said first trough in said base member, and said first and second ribs having at least one generally vertical surface that extends downward and generally perpendicular to said bottom surface of said insert member,
said one vertical surface of said first and second ribs having a mating interlocking and non-recurring geometric pattern formed in said at least one vertical surface of said first and second ribs, said mating pattern being adapted to selectively mate with said pattern of said base member when said insert member is mounted to engage said top surface of said base member, so as to provide only one mating position for said insert member on said base member,
a second trough formed in said base member at a location intermediate said first and second walls,
a third rib formed in said insert member at a mating location intermediate said first and second ribs, said mating location of said third rib allowing said third rib to reside in said second trough when said insert member is selectively mated with said base member, and
releasable insert locking means carried by said third rib and said second trough.
2. The dental handling apparatus of claim 1 wherein said second trough in said base member is located generally in the center of said first trough, and extends downward toward said bottom surface of said base member.
3. The dental handling apparatus of claim 2 including;
saw cut indicator means for a dental model, said saw cut indicator means being located in said base member at a vertical position that is intermediate said top and bottom surfaces of said base member.
4. The dental handling apparatus of claim 3 wherein said first, second and third ribs in said insert member extend vertically downward, and terminate at a position that is vertically above said saw cut indicator means.

5. The dental handling apparatus of claim 4 wherein said third rib of said insert includes a generally horizontal bottom surface, said apparatus including;
   a plurality of generally vertically upward extending holes formed in said bottom surface of said third rib of said insert, each of said holes being adapted to receive a dental dowel pin, and
   said second trough in said base member being dimensioned to receive dowel pins inserted in said holes.

6. The dental handling apparatus of claim 5 comprising a left jaw quadrant base member constructed in accordance with claim 5, a right jaw quadrant base member constructed in accordance with claim 5, a left jaw quadrant insert member constructed in accordance with claim 5, and a right jaw quadrant insert member constructed in accordance with claim 5, and including;
   mating coupling means formed in said left and right base members facilitating the coupling of said left and right base members in only one position, to thereby form a dental handling tool for both the left and right jaw full arch quadrants.

7. The dental handling apparatus of claim 1 wherein said top surface of said insert member includes;
   upward extending projections adapted to be imbedded in a non-hardened dental model positioned on said top surface of said insert member, and
   a manually removable wall member surrounding and containing a non-hardened dental model, said wall being adapted to be manually removed after hardening of the dental model.

8. The dental handling apparatus of claim 7 wherein said first and second troughs, and said first, second and third ribs have an arcuate shape approximating a dental quadrant.

9. The dental handling apparatus of claim 8 wherein said second trough in said base member is located generally in the center of said first trough, and extends downward toward said bottom surface of said base member.

10. The dental handling apparatus of claim 9 including;
   saw cut indicator means for a dental model, said saw cut indicator means being located in said base member at a vertical position that is intermediate said top and bottom surfaces of said base member.

11. The dental handling tool of claim 10 wherein said first, second and third ribs in said insert member extend vertically downward and terminate at a position that is vertically above said saw cut indicator means.

12. The dental handling apparatus of claim 11 wherein said third rib of said insert includes a generally horizontal bottom surface, said apparatus including;
   a plurality of generally vertically upward extending holes formed in said bottom surface of said third rib of said insert, each of said holes being adapted to receive a dental dowel pin, and
   said second trough in said base member being dimensioned to receive dowel pins inserted in said holes.

13. The dental handling tool of claim 12 comprising a left jaw quadrant base member constructed in accordance with claim 12, a right jaw quadrant base member constructed in accordance with claim 12, a left jaw quadrant insert member constructed in accordance with claim 12, and a right jaw quadrant insert member constructed in accordance with claim 12, and including;
   mating coupling means formed in said left and right base members facilitating the coupling of said left and right base members in only one position, to thereby form a dental handling tool for both the left and right jaw full arch quadrants.

14. The dental handling tool of claim 1 wherein said base member and said insert member are formed of dimensionally stable plastic resin material that retains its rigidity in thin wall construction while being easily manually cut by a saw blade.

15. The dental handling tool of claim 14 wherein said plastic resin material is polystyrene.

16. The dental handling apparatus of claim 15 wherein said third rib of said insert includes a generally horizontal bottom surface, said apparatus including;
   a plurality of generally vertically upward extending holes formed in said bottom surface of said third rib of said insert, each of said holes being adapted to receive a dental dowel pin, and
   said second trough in said base member being dimensioned to receive dowel pins inserted in said holes.

17. The dental handling tool of claim 16 comprising a left jaw quadrant base member constructed in accordance with claim 16, a right jaw quadrant base member constructed in accordance with claim 16, a left jaw quadrant insert member constructed in accordance with claim 16, and a right jaw quadrant insert member constructed in accordance with claim 16, and including;
   mating coupling means formed in said left and right base members facilitating the coupling of said left and right base members in only one position, to thereby form a dental handling tool for both the left and right jaw full arch quadrants.

* * * * *